(12) United States Patent
Maxfield et al.

(10) Patent No.: US 11,318,259 B2
(45) Date of Patent: May 3, 2022

(54) NEEDLE SHIELD REMOVER

(71) Applicant: SHL MEDICAL AG, Zug (CH)

(72) Inventors: Brian Maxfield, Delray Beach, FL (US); Dane Kris, Deerfield Beach, FL (US); Jason Frost, Boca Raton, FL (US)

(73) Assignee: SHL MEDICAL AG, Zug (CH)

( * ) Notice: Subject to any disclaimer, the term of this patent is extended or adjusted under 35 U.S.C. 154(b) by 188 days.

(21) Appl. No.: 16/607,283

(22) PCT Filed: Apr. 23, 2018

(86) PCT No.: PCT/EP2018/060342
§ 371 (c)(1),
(2) Date: Oct. 22, 2019

(87) PCT Pub. No.: WO2018/202459
PCT Pub. Date: Nov. 8, 2018

(65) Prior Publication Data
US 2021/0001055 A1    Jan. 7, 2021

Related U.S. Application Data

(60) Provisional application No. 62/492,589, filed on May 1, 2017.

(51) Int. Cl.
*A61M 5/32*    (2006.01)

(52) U.S. Cl.
CPC ................................ *A61M 5/3204* (2013.01)

(58) Field of Classification Search
CPC ........ A61M 5/3204; A61M 2005/3117; A61M 5/24; A61M 5/32
See application file for complete search history.

(56) References Cited

U.S. PATENT DOCUMENTS

| 2012/0216335 A1 | 8/2012 | McKenna, Jr. et al. |
| 2016/0354550 A1* | 12/2016 | Ward .................... A61M 5/326 |

FOREIGN PATENT DOCUMENTS

| CN | 201154127 Y | 11/2008 |
| CN | 201186089 Y | 1/2009 |
| CN | 102971024 A | 3/2013 |
| CN | 103415314 A | 11/2013 |
| CN | 204336970 U | 5/2015 |
| CN | 104968384 A | 10/2015 |
| CN | 105848698 A | 8/2016 |
| EP | 0518397 A1 | 12/1992 |

(Continued)

OTHER PUBLICATIONS

International Search Report and Written Opinion for Int. App. No. PCT/EP2018/060342, dated Jul. 16, 2018.

*Primary Examiner* — Brandy S Lee
(74) *Attorney, Agent, or Firm* — McDonnell Boehnen Hulbert & Berghoff LLP

(57) ABSTRACT

A needle shield remover is presented having a generally tubular body with a longitudinal extension and a grip element composed of a braided sleeve arranged to the tubular body, where the braided sleeve has an opening of such a diameter that a needle shield may be introduced, where the diameter narrows such that a friction fit is created between the braided sleeve and the needle shield when said needle shield is pulled for removing the needle shield.

12 Claims, 2 Drawing Sheets

(56) References Cited

FOREIGN PATENT DOCUMENTS

| EP | 2878322 A1 | 6/2015 | |
|---|---|---|---|
| EP | 3108915 A1 | 12/2016 | |
| FR | 3024040 A1 | 1/2016 | |
| WO | 2017/139377 A1 | 8/2017 | |
| WO | WO-2017139377 A1 * | 8/2017 | .......... A61M 5/3204 |

* cited by examiner

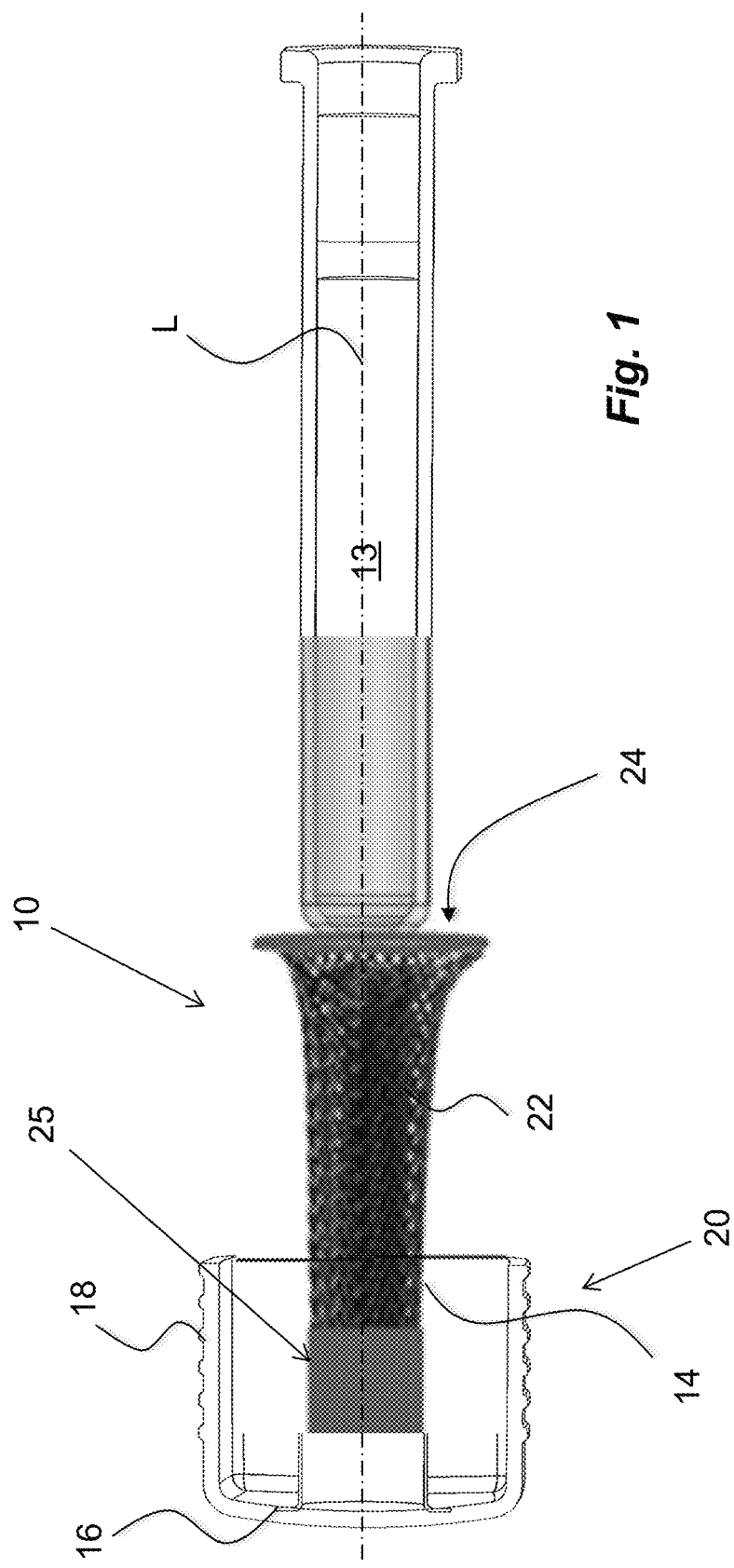

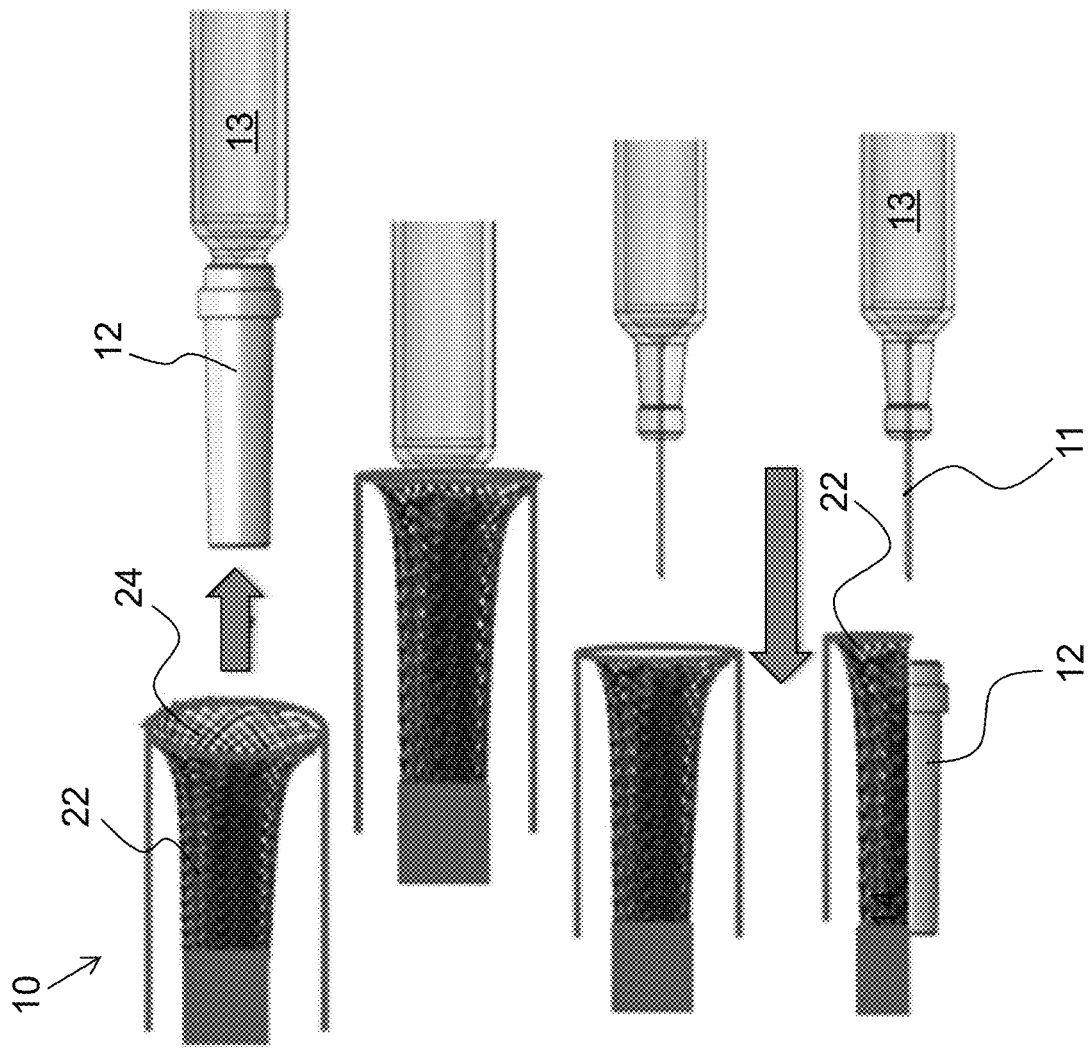

NEEDLE SHIELD REMOVER

CROSS REFERENCE TO RELATED APPLICATIONS

The present application is a U.S. National Phase Application pursuant to 35 U.S.C. § 371 of International Application No. PCT/EP2018/060342 filed Apr. 23, 2018, which claims priority to U.S. Provisional Patent Application No. 62/492,589 filed May 1, 2017. The entire disclosure contents of these applications are herewith incorporated by reference into the present application.

TECHNICAL AREA

The present disclosure relates to a needle shield remover.

BACKGROUND

A large number of medicament delivery devices that are designed for self-medication are arranged with prefilled syringes or the like medicament containers that in turn are provided with medicament delivery members such as injection needles. In order to keep the injection needles sterile, a needle shield is often attached to and surrounds the needle. One very common type of needle shield is a so called flexible needle shield or FNS. The FNS is often made of a resilient material such as rubber, having an inner cavity in which the needle is placed. The dimensions of the cavity are chosen such that a tight fit is obtained around the needle, thereby preventing any contamination of the sterile needle.

However, the tight fit means that there is a friction fit, thus requiring some force in order to pull the needle shield off the needle. Many medicament delivery devices are therefore provided with needle shield removers, which in turn often are attached to safety caps at a proximal end of the medicament delivery device. The safety cap is in that regard arranged with a grip part so that the user may be provided with a good grip for the pulling action.

The needle shield removers may have different designs. Often they have a generally tubular body with a diameter that is somewhat larger than the diameter of the needle shield so that the body may fit around the needle shield coaxially. Different types of grip elements on the body have been developed for providing a proper grip of the surface of the needle shield so that it may be removed when pulling the safety cap, against the friction force. Different types of grip elements have entailed tongues, protrusions and other types of contact elements that engage with the outer surface of the needle shield. Many of these solutions display drawbacks such as varying grip capabilities due to tolerance differences between engaging components, difficulties in obtaining a good grip on the rubber material of the FNS, complicated manufacturing and/or assembly, just to mention a few drawbacks. Similar problems occur with rigid needle shields, RNS, wherein an inner needle shield of a flexible material is provided with an outer housing or shell of a more rigid material. The challenges of gripping such an RNS are more or less the same as for FNS even though the material properties of the outer surfaces are different. There is thus room for improvement of needle shield removers for removing needle shields.

SUMMARY

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the device is located closest to the medicament delivery site of the patient.

The aim of the disclosed needle shield remover is to remedy the drawbacks of the state of the art removers. This aim is solved by a needle shield remover with the features according to the independent patent claims. Preferable embodiments of the needle shield remover form the subject of the dependent patent claim.

According to one feature of the disclosed needle shield remover, it comprises a generally tubular body having a longitudinal extension. The body is further arranged with a grip element comprising a braided sleeve. The braided sleeve may preferably have an opening with such a diameter that a needle shield may be introduced. Further, the braided sleeve may have such a diameter that a friction fit is created between the braided sleeve and the needle shield when the needle shield remover is pulled off for removing the needle shield. The advantage with this solution is that a large part of the inner surface of the braided sleeve will create the friction fit. There are thus no discrete elements that form the contact between the needle shield remover and the needle shield, but a major part of the inner surface, thus increasing the capability of removing the needle shield that is friction fit around an injection needle.

In order to enhance the contact area and thus enhance the friction fit between the needle shield remover and the needle shield the braided sleeve may have such an extension in the longitudinal direction in relation to a length of the needle shield that the braided sleeve covers generally the length of the needle shield when mounted. It may also be that the length of the braided sleeve is longer than the length of the needle shield. Further, in order to ensure a good friction fit between the needle shield remover and the needle shield the braided sleeve may be contractable when pulled in a longitudinal direction.

The needle shield remover may have a braided sleeve that is made of a plastic material. Alternatively the braided sleeve may be made of a metallic material. The choice of material may depend on the desired function and/manufacturing aspects. Further, the body may be arranged with attachment elements for a grip part of a protective cap.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 1 is a cross-sectional view of a medicament container provided with a needle shield remover of a protective cap, and FIG. 2 is a perspective schematic view of a first starting position of the needle shield remover in relation to the needle shield and medicament container.

FIG. 3 is a schematic view of a second consequent position of the needle shield remover being placed onto the needle shield.

FIG. 4 is a schematic view of a third position of the needle shield remover being moved proximally as indicated by an arrow.

FIG. 5 is a schematic partial cross-sectional view of the needle shield remover in the third position being removed and illustrating the retained needle shield inside the needle shield remover.

DETAILED DESCRIPTION

The disclosure pertains to a needle shield remover 10 that is to be used with for example a medicament delivery device. Before use of the medicament delivery device, an injection needle 11 of a medicament container 13, FIGS. 1 and 2, is protected by a needle shield 12, and often by a so called flexible needle shield, or FNS or a rigid shield remover, or RNS. The FNS is in this regard made of a soft, resilient material such as rubber and the RNS is provided with an outer shell or casing of a rigid material. In order to perform an injection, the needle shield has to be removed. In that regard, the medicament delivery device is arranged with a needle shield remover 10, FIG. 1.

In the embodiment shown in the figures, the needle shield remover 10 comprises a generally tubular body 14, FIG. 1, extending in a longitudinal direction L. At a proximal end of the body 14, attachment elements 16 may be arranged that may be designed to fit with a grip part 18 of a protective cap 20 of a medicament delivery device (not shown) that is designed so that a user can grip the cap 20 and pull off together with the needle shield 12. As an alternative, the body 14 may be made integrally with the grip part 18 of the cap 20.

The needle shield remover 10 of the embodiment further comprises a grip portion 22, FIG. 1, that is to interact with the needle shield 12. The grip portion 22 comprise a sleeve of a braided material, wherein the sleeve 22 has a distally directed opening 24 having a first diameter such that the needle shield may enter into the sleeve in a first state. The braided sleeve 22 is designed such that it may be stretched contracting in the diameter and thus provide a reduced inner second diameter when pulled in a longitudinal direction. The braided sleeve 22 may be made of metal or plastic and even reinforced with suitable fibres. The proximal end of the braided sleeve 22 may have a ring 25 of a more rigid material, alternatively the end of the braided sleeve 22 is heat treated to form the ring 25 integral with the body 14.

When the needle shield remover 10 according to the described embodiment is to be attached to the needle shield 12, it is pushed with the distal opening 24 of the braided sleeve 22 in the first relaxed state towards a distal end surface of the needle shield 12, FIG. 2. The taper of the needle shield 12 and the flexibility of the braided sleeve 22 will allow it to slide along and form around the outer surface of the needle shield 12, FIG. 3. Preferably the length of the braided sleeve 22 is such that the whole length of the needle cover or the needle shield 12 is covered when the braided sleeve 22 has been placed around the needle shield 12. It might also be that the braided sleeve 22 extends further than the length of the needle shield 12.

When the medicament delivery device is to be used, a user grabs the grip part 18 of the protective cap 20 to which the needle shield remover 10 is attached via a flange. The protective cap 20 with the needle shield remover 10 is now pulled in the proximal direction. When now the braided sleeve 22 is pulled in the proximal direction, it will be stretched in the second state, contracted around a circumference of the needle shield 12 decreasing its diameter and creating a tight frictional connection so that the needle shield 12 is tightly held and also pulled in the proximal direction, exposing the injection needle 11, as illustrated in FIGS. 4 and 5, whereby the medicament delivery device (only partly illustrated) is ready for penetration at a dose delivery site.

It is to be understood that the embodiment described above and shown in the drawings is to be regarded only as a non-limiting example of the disclosure and that it may be modified in many ways within the scope of the patent claims.

The invention claimed is:

1. A needle shield remover, comprising:
   a generally tubular body; and
   a protective cap having an outside surface including a grip part, wherein an inside surface of the protective cap is connected to a proximal end of the generally tubular body,
   wherein the generally tubular body comprises a first portion at a distal end of the generally tubular body and a second portion at the proximal end of the generally tubular body, wherein the first portion comprises a braided sleeve having an opening at a distal end of the generally tubular body with a first diameter such that a needle shield which is friction fit around an injection needle may be inserted into the opening, wherein the braided sleeve has a second diameter proximal to the distal end of the generally tubular body of such a size that a friction fit is created between the braided sleeve and the needle shield when said protective cap is pulled in a proximal longitudinal direction to thereby remove the needle shield from a medicament container, wherein the second portion of the generally tubular body comprises a ring, and wherein the ring comprises a material that is more rigid than a material of the braided sleeve.

2. The needle shield remover according to claim 1, wherein the braided sleeve has length that extends in a longitudinal direction such that the braided sleeve covers generally the length of the needle shield when the needle shield is positioned inside of the braided sleeve.

3. The needle shield remover according to claim 1, wherein the braided sleeve is contractable when pulled axially in a longitudinal direction.

4. The needle shield remover according to claim 1, wherein the second diameter reduces in size when the braided sleeve is pulled axially in a longitudinal direction.

5. The needle shield remover according to claim 1, wherein the braided sleeve is made of a plastic material.

6. The needle shield remover according to claim 1, wherein the braided sleeve is made of a metallic material.

7. The needle shield remover according to claim 1, wherein the generally tubular body further comprises an attachment element that connects to the protective cap.

8. The needle shield remover according to claim 7, wherein the attachment element comprises a flange.

9. The needle shield remover according to claim 1, wherein the generally tubular body is formed as an integral part of the protective cap.

10. The needle shield remover according to claim 1, wherein the ring is formed as an integral part of the generally tubular body.

11. The needle shield remover according to claim 1, wherein the grip part is configured so that a user can grip the protective cap to pull off the needle shield using the braided sleeve.

12. The needle shield remover according to claim 1, wherein the generally tubular body comprises a non-braided portion that is connected to the inside surface of the protective cap.

* * * * *